(12) United States Patent
Klimyuk et al.

(10) Patent No.: US 7,247,768 B1
(45) Date of Patent: Jul. 24, 2007

(54) METHOD OF MAKING PLANT ARTIFICIAL CHROMOSOMES

(75) Inventors: Victor Klimyuk, Halle (DE); Nickolay V. Kuchuk, Kiev (UA)

(73) Assignee: Icon Genetics, Inc., Princeton, NJ (US)

(*) Notice: Subject to any disclaimer, the term of this patent is extended or adjusted under 35 U.S.C. 154(b) by 99 days.

(21) Appl. No.: 10/030,793

(22) PCT Filed: Aug. 7, 2000

(86) PCT No.: PCT/US00/21461

§ 371 (c)(1),
(2), (4) Date: Jan. 11, 2002

(87) PCT Pub. No.: WO01/11020

PCT Pub. Date: Feb. 15, 2001

Related U.S. Application Data

(60) Provisional application No. 60/147,445, filed on Aug. 5, 1999.

(51) Int. Cl.
*C12N 15/82* (2006.01)
*C12N 5/14* (2006.01)
*A01H 1/00* (2006.01)
*A01H 5/00* (2006.01)
*A01H 5/10* (2006.01)

(52) U.S. Cl. .................................. 800/278; 800/269

(58) Field of Classification Search ............ 435/419, 435/70.2, 468, 483; 800/260, 266, 267, 268, 800/269, 270, 277, 280, 295, 298
See application file for complete search history.

(56) References Cited

U.S. PATENT DOCUMENTS 5,270,201 A    12/1993   Richards et al. ........... 536/23.1

FOREIGN PATENT DOCUMENTS

WO    WO-98/55637 A1    12/1998

OTHER PUBLICATIONS

Famelaer et al., Theor. Appl. Genet., 1990, vol. 79, pp. 513-520.*
Blume et al., Plant Journal, 1997, vol. 12, pp. 731-746.*
Adam et al., Plant J., 1997, vol. 11, pp. 1349-1358.*
Sanford et al., Theor. Appl. Genet., 1984, vol. 67, pp. 553-558.*
Chyi et al., Theor. Appl. Genet., 1985, vol. 70, pp. 433-439.*
Pandey, Theor. Appl. Genet., 1986, vol. 72, pp. 739-742.*
Lee et al., J. Am. Chem. Soc., 1992, vol. 114, pp. 985-997.*
Golik et al., J. Am. Chem. Soc., 1987, vol. 109, pp. 3461-3462.*
G. Suzuki, et al., "Direct Cloning Of The Brassica S Locus By Using A P1-Derived Artificial Chromosome (PAC) Vector", Vector. Gene vol. 199, pp. 133-137, 1997.
T. Quonzhou, et al., Cloning And Stable Maintenance Of DNA Fragments Over 300 kb In *Escherichia coli* With Conventional Plasmid-Based Vectors, Nucl. Acids Res., vol. 26, No. 21, pp. 4901-4909, 1998.
de Kochko, Cahier Agricultures, 9(4):287-292 (2000).
Pandey, Nature, vol. 256, No. 5515, Jul. 24, 1975, pp. 310-313.

* cited by examiner

*Primary Examiner*—Ashwin Mehta
(74) *Attorney, Agent, or Firm*—Lerner, David, Littenberg, Krumholz & Mentlik, LLP

(57) ABSTRACT

Disclosed are methods of making plant artificial chromosomes. In one embodiment, the method entails: (a) preparing recombinant protoplasts of a first plant species containing an exogenous nucleic acid (e.g., DNA) of interest; (b) producing chromosome fragments of chromosomes contained in the recombinant protoplasts; (c) fusing the recombinant protoplasts of (b) with protoplasts of a second plant species to produce fused protoplasts, wherein the first and second plant species may be the same or different; and (d) identifying fused protoplasts of (c) or cells derived from the fused protoplasts of (c) that contain chromosome fragments that exhibit normal plant chromosomal properties. The chromosome fragments may be moved from one plant species to another. Whole plants, plant cell cultures and intermediates of same are also provided.

18 Claims, 4 Drawing Sheets

METHOD OF MAKING PLANT ARTIFICIAL CHROMOSOMES

CROSS REFERENCE TO RELATED APPLICATIONS

The present application is a national phase entry under 35 U.S.C. §371 of International Application PCT/US00/21461, filed Aug. 7, 2000, which claims benefit of U.S. Provisional Patent Application 60/147,445, filed Aug. 5, 1999. The disclosures of all of said applications are incorporated by reference herein.

TECHNICAL FIELD

The present invention relates to the field of molecular genetics and particularly to the production of artificial chromosomes such as plant artificial chromosomes.

BACKGROUND OF THE INVENTION

Several methods have been developed for the introduction and expression of genes in plant and animal cells and particularly plant cells. These methods have a number of limitations, especially considering the complexity of the breeding process required for the introgression of more than a few genes into elite lines and obtaining stable, predictable expression of the individual genes. The current methods for plant transformation are limited to the introduction of small segments of DNA, generally sufficient for the expression of two to three genes. With the rapid increase in rate of sequencing and the discovery of new genes for modifying agronomic traits and for directing plants to synthesize material from entirely new pathways, this limitation will be severely limiting. In addition, the current method of randomly introducing genes into the genome of the recipient plant leads to extensive linkage drag, potential for disruption of important genes and confounding the production of elite lines.

The artificial chromosome is a linear piece of DNA that contains all the necessary elements for stable replication and segregation. Artificial chromosomes have been described for yeast (Burke et al., Science 236:806-812, (1987)), bacteria (O'Connor et al., Science 244(4910):1307-1312 (1989), Shizuya et al., Proc. Natl. Acad. Sci. USA 89(18):8794-8797 (1992), Hosoda et al., Nucleic Acids Res. 18(13):3863-3869 (1990)), and more recently for animals (Harrington et al., Nature Genetics 15:345-355 (1998); Grimes and Cooke, Human Molecular Genetics 7(10):1635-1640 (1998); and Ikeno et al., Nature Biotechnology 16:431-439 (1998)). In these cases, the chromosomes were produced by identifying the required elements and then manipulating them to build a chromosome, or via in vivo and in vitro manipulations involving isolation of one or more chromosomal elements.

U.S. Pat. No. 5,270,201 describes telomeric sequences from *Arabidopsis* and use of those sequences to construct a plant artificial chromosome. The patent disclosure relates to a recombinant DNA molecule that contains the telomere and optionally the centromere of a higher eukaryote. To provide a functional artificial chromosome in accordance with the teachings of the patent, the functional elements of a chromosome must be assembled and transformed into a plant cell. The element exemplified in the patent, the telomere, is the simplest one of the necessary pieces. Presently however, a plant centromere is known to be a highly complex structure of at least 360,000 base pairs. More recently, PCT application (WO 98/55637) describes the identification and cloning of functional plant centromeres based on *Arabidopsis*.

Hence, there is a need in the agricultural biotechnology arts for methods of producing plant artificial chromosomes that entail less complex genetic manipulation and assembly of individual chromosomal elements.

SUMMARY OF THE INVENTION

Applicants have invented methods of producing plant artificial chromosomes. The method is generally applicable to any plant species of interest including dicots and monocots. The methods take advantage of the natural ability of a plant cell to repair damage done to its chromosomes. Rather than synthesize artificial chromosomes from known functional chromosomal elements such as centromeres, telomeres and autonomously replicating sequences, the present invention utilizes the normal metabolic functions of a plant cell to perform all necessary processes to create functional minichromosomes.

A first aspect of the present invention is directed to a method of making a plant artificial chromosome. It entails the following:

a) preparing recombinant protoplasts of a first plant species containing an exogenous or non-native nucleic acid (e.g., DNA) of interest; b) producing chromosome fragments of chromosomes contained in the recombinant protoplasts; c) fusing the recombinant protoplasts of (b) with protoplasts of a second plant species to produce fused protoplasts, wherein the first and second plant species may be the same or different; and d) identifying fused protoplasts of c) or cells derived from the fused protoplasts of (c) that contain chromosome fragments that exhibit normal plant chromosomal properties.

In another embodiment, the plant artificial chromosome is made by the following procedure:

a) producing transformed plants of a first plant species containing an exogenous nucleic acid; b) producing chromosome fragments of chromosomes of the first plant species; c) crossing the first plant species containing the chromosome fragments with a second plant species to produce hybrid plant species wherein the first and second plant species may be the same or different; and d) identifying hybrid plant species of c) or cells or protoplasts thereof containing at least one chromosome fragment that exhibits normal plant chromosomal functions.

In preferred embodiments, chromosome fragments are produced by irradiating the protoplasts or treating with a chemical agent. Fused protoplasts or cells derived from the fused protoplasts that contain chromosome fragments exhibiting normal plant chromosomal properties are identified by pulsed field gel electrophoresis. The first and second plants may be members of the same species or family, or they may be unrelated. The methods are applicable to all plants—monocots and dicots alike.

In other preferred embodiments, the exogenous DNA contains at least one functional site such as a recombination site, a restriction site and/or a coding region. Selectable marker genes are generally included as a part of the coding region. Yeast chromosomal elements, e.g., yeast artificial chromosomes, are preferred. In these cases, wherein the coding region contains a centromeric sequence functional in a yeast cell, the method of the present invention produces a chromosomal fragment containing another centromeric sequence functional in a plant cell, as well as the centromeric sequence functional in a yeast cell. These DNAs are reconstructed into a recombinant or shuttle vector and are used to produce transformed or recombinant plant or yeast cells. More generally, however, the plant artificial chromosomes (PACs) produced by the presently disclosed methods, and constructs and cells transformed with the PACs, are also provided.

Another aspect of the present invention is directed to whole plants produced by the methods, such as by regenerating the plants from the fused protoplasts. Isolated plant cells and plant cell and protoplast cultures are also disclosed.

A further aspect of the present invention is directed to a method of making a transgenic plant. This method entails a) preparing recombinant protoplasts of a first plant species containing an exogenous nucleic acid; b) producing chromosome fragments of chromosomes contained in the recombinant protoplasts; c) fusing the recombinant protoplasts of (b) with protoplasts of a second plant species to produce fused protoplasts, wherein the first and second plant species may be the same or different; d) identifying fused protoplasts of c) or cells derived from the fused protoplasts of (c) that contain chromosome fragments that exhibit normal plant chromosomal properties; and e) regenerating a whole plant from the protoplasts or cells identified in d) that contain the chromosome fragments exhibiting normal plant chromosomal properties. Seed derived from the transgenic plants is also provided.

DETAILED DESCRIPTION OF THE INVENTION

Figure 1:
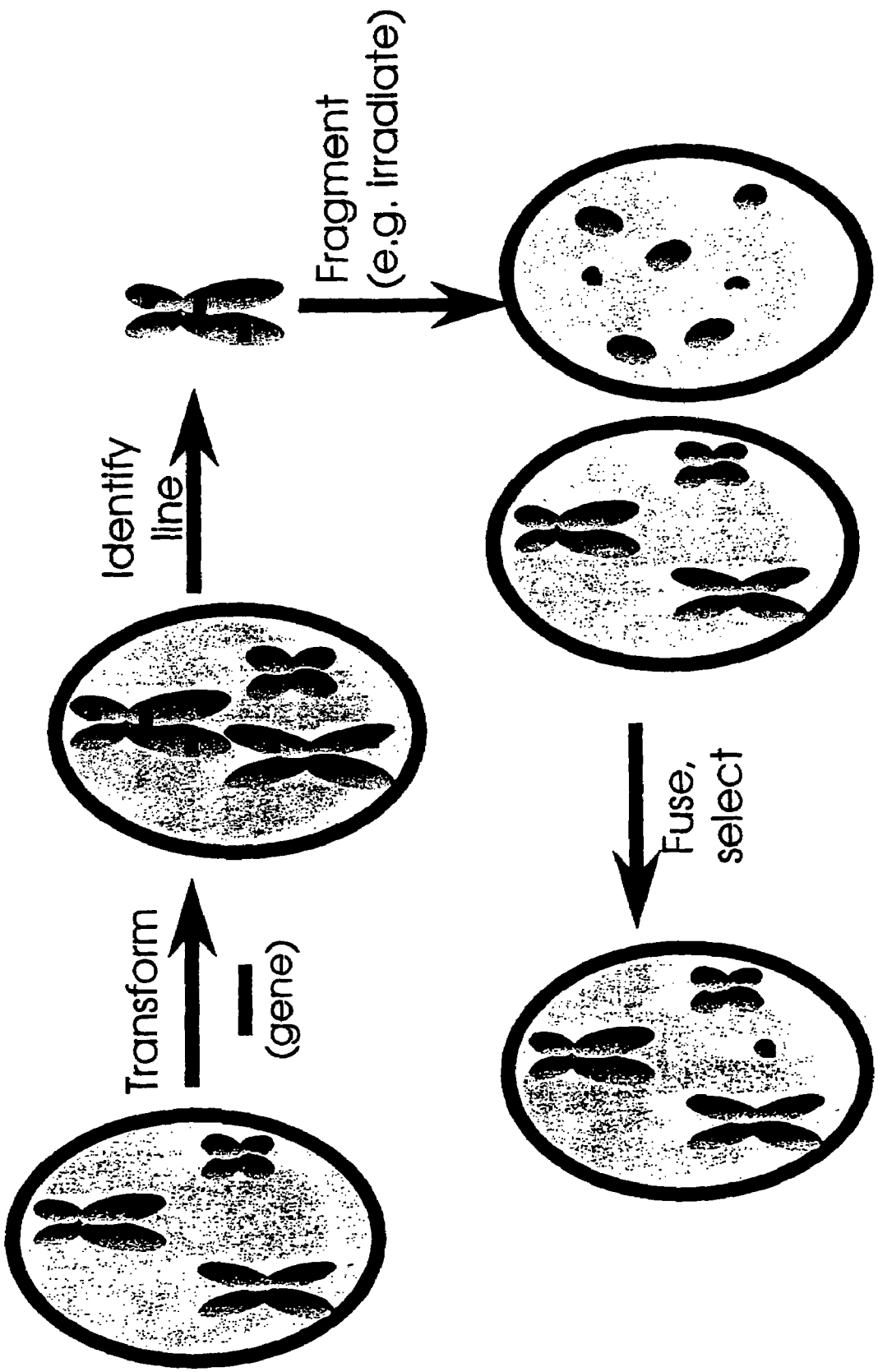
FIG. 1 is a schematic presentation of the in vivo generation of plant artificial chromosomes in accordance with the present invention.

The invention relates to the production of artificial chromosomes and the preparation of cell lines containing functional artificial chromosomes. Also provided are methods for introducing DNA into the artificial chromosome by targeted integration and delivery of the artificial chromosome into recipient cells. Cells that can harbor and that can be used in the manipulation of the artificial chromosome include yeast and cells from monocotyledonous and dicotyledonous plants, and the cell cultures and regenerated plants from those cells.

The telomere is a stretch of DNA at the ends of chromosomes that are required for the complete replication of the chromosomal ends. A eukaryotic chromosome would shorten after each round of replication except for the presence of the telomere at each end. The telomere has a characteristic DNA sequence that is replicated differently from the bulk of the chromosome. The telomere serves as primer for the completion of the lagging strand as the chromosome replicates.

Isolation of the first eukaryotic telomere was accomplished in 1988 from *Arabidopsis*. Studies of the *Arabidopsis* telomeres showed that the structure of this DNA is very similar to that seen in lower eukaryotes. Telomere structure appears to be well conserved throughout the angiosperms. The telomeres of the monocot maize are varied in size and cross-hybridize with the telomeric sequence of *Arabidopsis*. The conservation of telomere structure and sequence is also seen into the animal kingdom.

The centromere is required for the accurate segregation of the sister chromatids after replication. The centromere consists of a sequence that is distinct from the rest of the chromosome. Kinetochores, which form at the centromere, attach to the spindle during mitosis and meiosis and are responsible for separation of the chromosomes. Centromeres are typically composed of large arrays of tandemly repeated DNA families. See, Clarke, Curr. Opin. Gen. Dev. 8:212-218 (1998) and Pidoux, et al., Curr. Opin. Cell Biol. 12:308-319 (2000).

The DNA fragments conferring the function of autonomously replicating sequences (ARS) have been isolated and characterized from many plant species. See, Berlani et al., Plant Mol. Biol., 11:161-162 (1988); Hernandes et al., Plant Mol. Biol., 10:413-422 (1988); Berlani et al., Plant Mol. Biol., 11:173-182 (1988); and Eckdahl et al., Plant Mol. Biol., 12:507-516 (1989). ARS elements from genomes of higher plants have structural and sequence features in common with ARS elements from yeast and higher animals (Eckdahl et al., Plant Mol. Biol., 12:507-516 (1989)). The plant ARS elements are capable of conferring autonomous replicating ability to plasmids in *Saccharomyces cerevisiae*. Study of maize nuclear DNA sequences capable of promoting the autonomous replication of plasmids in yeast showed that they represent two families of highly repeated sequences within the maize genome. Those sequences have characteristic genomic hybridization patterns. There was typically only one copy of an ARS-homologous sequence on each 12-15 kb of genomic fragment (Berlani et al., Plant Mol. Biol., 11:161-162 (1988)).

In accordance with one embodiment of the presently disclosed invention, a plant artificial chromosome (PAC) is produced first by introducing the exogenous DNA e.g., one or more gene(s) of interest including or associated with a selectable marker gene, into the desired plant species (e.g., maize). The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing, et al., Gene 19:259-268 (1982); Bevan, et al., Nature 304:184-187 (1983)), the bar gene which confers resistance to the herbicide phosphinothricin (White, et al., Nucl. Acids Res. 18:1062 (1990); Spencer, et al., Theor. Appl. Genet. 79:625-631 (1990)), the hph gene which confers resistance to the antibiotic hygromycin (Blochinger, et al., Mol. Cell. Biol. 4:2929-2931)), and the dhfr gene, which confers resistance to methotrexate. Vectors suitable for *Agrobacterium* transformation typically carry at least one T-DNA border sequence. These include vectors such as pBIN19 and pCIB200 (EP 0 332 104).

Stable transformed cell lines are then selected which express the exogenous or non-native nucleic acid. The cells may be either from a whole regenerated plant following transformation and selection, or the cells may be obtained from suspension culture following transformation and selection. Methods of transforming plant cells or protoplasts to integrate exogenous DNA in the plant chromosome may be performed in accordance with standard procedures. Choosing a specific technique will depend primarily on whether the plant is a monocot or dicot.

Transformation techniques for dicotyledons are well known in the art and include *Agrobacterium*-based techniques and techniques that do not require *Agrobacterium*. Non-Agrobacterium techniques involve the uptake of exogenous genetic material directly by protoplasts or cells. These techniques include PEG or electroporation mediated uptake, particle bombardment-mediated delivery and microinjection. Examples of these techniques are described in Paszkowski et al., EMBO J., 3:2717-2722 (1984), Potrykus et al, Mol. Gen. Genet 199:169-177 (1985), Reich et al., Biotechnology 4:1001-1004 (1986), and Klein et al., Nature, 327: 70-73 (1987). In each case, the transformed cells are regenerated to whole plants using standard techniques.

Preferred transformation techniques for monocots include direct gene transfer into protoplasts using PEG or electroporation techniques and particle bombardment into callus tissue. Transformation can be undertaken with a single DNA species or multiple DNA species (i.e., co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093-1096 (1986)).

Generation and Rescue of Minichromosomes

Protoplasts are derived from the transformed cells in accordance with standard techniques. In one preferred embodiment, fragments of the plant chromosomes (also referred to as "minichromosomes") are produced by irradiating the protoplasts. The irradiation renders the protoplasts non-viable. High doses of gamma radiation (e.g., 1000 Gy from a Cobalt-60 source) are particularly suitable. There are other methods from fragmenting chromosomal DNA. For example, the protoplasts or cells may be treated or otherwise contacted with a chemical agent. Examples of such agents include calicheamicin, esperamicin, dynemicin and neocarzinostatin. These agents are believed to mediate chromosomal cleavage via transient di-radical intermediates. See, Lee, et al., J Antibiot (Tokyo) 42(7):1070-87 (July 1989); Lee, et al., J. Am. Chem. Soc. 114:985(1982); and Golik, et al., J. Am. Chem. Soc. 109:3461 (1987).

The treated protoplasts are fused with non-transformed or normal (e.g., undamaged) protoplasts derived from cells of the same plant species or a different but related (i.e., the same family of) plant species, in accordance with standard techniques. The purpose of fusing the treated protoplasts with non-transformed protoplasts is to revive the transformed protoplasts from the effects of the chromosomal disruption e.g., caused by irradiation or chemical treatment.

The fused protoplasts are cultured on selective media to allow whole plant cells to form and to identify plant cells that contain and express the gene(s) of interest. These cells are screened by any suitable method (FISH, GISH, PFGE, Southern blot, etc.) to identify lines that have the gene of interest on a minichromosome that otherwise exhibits normal chromosomal activities. By "normal chromosomal activities", it is meant that the microchromosomes, artificial chromosome or chromosome fragments contain a centromere, telomeric and ARS sequences and are stable through normal cellular events such as meiosis and mitosis. That is, they are capable of independent replication and transmission through subsequent cell divisions.

After analyzing the stability of the desired microchromosome, it can be used as an artificial chromosome. This cell line or plant can be treated again as described above to select even smaller microchromosomes or PACs. The plant artificial chromosomes can be easily moved from one plant species to another by different means including methods based on unstable hybrid formation.

In a more preferred embodiment of this invention, the initial transformants are screened by appropriate means (e.g., FISH, RAPD, PFGE and linkage analysis) to identify cell lines that have the gene(s) of interest located near the centromeric region of a chromosome. This preferred embodiment not only provides a higher probability of recovering microchromosomes that contain the desired gene(s) but results in the selection of the shortest fragments that contain the exogenous DNA and exhibit normal chromosomal activities. In general, the size of the minichromosomes lies in the range of from about 3 to about 4 Mb.p.

Chromosome fragments that exhibit normal chromosomal activity and contain the exogenous DNA can be isolated from the protoplasts and then further manipulated on a genetic level to incorporate additional exogenous DNA material of interest, and then transformed into a plant of interest. The isolated PACs can be introduced into the selected plant species in accordance with standard techniques such as electroporation or protoplasts or PEG-mediated transformation. In other embodiments, however, the fragments are not isolated; rather, are moved from plant cell to plant cell by successive fusion with protoplasts of the selected plant species. In these embodiments, the plant species containing the chromosome fragments (the "donor") and the selected plant species (the "recipient") are chosen such that upon crossing, produce unstable progeny or demonstrate segregation preferential or sorting out. Suitable pairs of plants include the donor, *Tripsacum*, and as the recipient, maize, wheat, barley or oat. In another preferred embodiment, the donor is *Orychophragmus* and the recipient is a crucifer such as canola. Donor/recipient pairs in other preferred embodiments are as follows: *Glycine tomentella*/soybean; *Solanum phreja*/potato; maize/wheat; maize/barley; maize/oat; *Pennisetum*/wheat; *Pennisetum*/barley; *Hordeum bulbosum*/barley; *Hordeum bulbosum*/wheat; *Nicotiana diglutal*/*Nicotiana tabacum* and *Oryza minuta*/rice. Crossing the donor with the recipient plant is a viable technique provided that a fertile plant can be regenerated from a tissue culture carrying the PACs. Movement of the PACs from plant cell to yeast cell is accomplished by fusing the plant protoplast with a yeast spheroplast.

In another embodiment, a sexual cross between two plants is used not only to rescue chromosome fragments, but for their subsequent movement between different organisms as well. In this embodiment, transformed plants are produced as described. Instead of treating protoplasts, whole transgenic plants or pollen from a whole transgenic plant is treated with an agent, such as irradiation, to induce chromosome fragmentation. Such treated pollen is then used to pollinate a second plant. It has been shown (Pandey, Nature 256:310-313 (1975)) that crosses between irradiated and normal plants can be done and result in transfer of marker traits from the irradiated organism; the nature of such transgenosis has never been elucidated. The progeny from such crosses is analyzed and chromosome fragments that function as chromosomes are identified in the same way as chromosomes reconstructed through a protoplast fusion.

The exogenous nucleic acid varies widely. For example, it embraces any DNA not present in the native plant genome or in the desired copy number, and that encodes a protein whose expression in plants would be valuable from some standpoint. The DNAs and proteins fall into the broad categories of crop protection, crop improvement, production of specialty compounds including specific chemicals, nutraceuticals and other products associated with food quality such as modified starch, oils and protein compositions, that, in total, require the expression of a coordinate set of genes and thus a specialized transformation system in order to have the plant exhibit the trait of interest. An example is the isoprenoid biosynthetic pathway that is not regulated by plants. All genes involved in mevalonate biosynthesis—HMG-CoA synthase, HMG-CoA reductase, mevalonate kinase, phosphomevalonate kinase, mevalonate pyrophosphate carboxylase and isopentenyl pyrophosphate isomerase—are well known. Other examples are the genes involved in amino acid synthesis. The exogenous genes can be useful for modifying the input requirements of a plant such as their response to the environment, their ability to protect themselves from pests, protection from xenobiotic agents, which alter other traits such as overall yield, production of nutritionally balanced protein, better quality starch, high quality or quantity of oil or vitamin levels. The genes may also allow the plants to perform functions they normally do not such as to produce pharmaceutical proteins, antigens and small molecules.

In addition to the gene or genes that are intended to provide a recipient of the plant artificial chromosome with one or more traits of interest, it is preferred that the exogenous nucleic acid is organized in such a fashion to include more characteristics e.g., recombination sites for introducing new genes, components of a yeast artificial chromosome (YAC) such as telomeric sequences and an autonomous replicating sequence and preferably these elements in combination with a centromere, which import yeast-plant shuttle characteristics to the PAC, low frequency restriction enzyme sites for subsequent cloning, and other properties that facilitate subsequent manipulation in vitro. The presence of the YAC sequences allows further selection for the presence of artificial chromosomes and for performing genetic manipulations with them. The artificial chromosomes can be transferred to yeast for re-designing, e.g. equipping with the sequences of interest, including those for site-specific homologous recombination, and put back into the plant cells. See, U.S. Pat. Nos. 5,270,201; 5,288,625; 5,721,118; and 5,712,134. Yeast possess an efficient homologous recombination system that facilitates the DNA manipulation within yeast cells (Spencer et al., In Methods: a companion to Methods Enzymol. 5:161-175, (1993); Hieter et al., in Genome analysis: genetic and physical mapping. Ed. Davies, Tilghman. Cold Spring Harbor: C S H Laboratory Press, 1:83-120, (1990)). Actually as little as 30 bp of a homologous sequence at each end of a DNA fragment is sufficient to integrate the fragment into a linearized plasmid in yeast (Hua et al., Plasmid, 28:91-96 (1997)). Development of a yeast artificial chromosome (YAC) makes manipulation with foreign DNA even more convenient. YACs can tolerate more than 2 Mb of DNA inserts (Burke et al., Science, 236:806-812 (1987)). Plant minichromosomes carrying plant selectable markers and YAC sequences might serve as a shuttle vector that can be transferred from the plant cells into yeast for genetic manipulation and then be returned into the plant cell. By using a homologous recombination system, this shuttle vector can be equipped with any genes of interest, sequences recognized by site-specific recombinases (FLP, R, Cre), or additional selectable markers. Alternatively, large fragments of plant minichromosomes can be deleted or replaced with other sequences (Spencer et al., in *Methods: a companion to Meth. Enzymol.* 5:161-175 (1993)). It also allows preparative isolation of plant minichromosomes for further manipulations such as subcloning and sequencing or re-introduction into the plant cells with the help of microinjection, lipofection or electroporation. However, these transformation methods might have a technical barrier for obtaining sufficient amounts of intact DNA. Direct introduction of YAC DNA by cell fusion was reported for mammalian cells (Pavan et al., Mol. Cell. Biol. 10:4163-4169 (1990); Pachnis et al., Proc. Natl. Acad. Sci USA, 87:5109-5113, (1990)) as well as for plant protoplasts (Hatsuyama et al., Plant Cell Physiol. 35:93-98 (1994). The latter method allows transferring the DNA of interest from yeast into a plant cell by the means of yeast spheroplast-plant protoplast fusion, thus avoiding DNA fragmentation. The same approach can be used for the minichromosomes transfer from plant cells into the yeast. Thus, the minichromosomes carrying all elements necessary for independent maintenance in plant and yeast cells display all features of plant-yeast shuttle vector.

Site-specific recombinases from bacteriophage and yeasts are being widely used as tools for manipulating DNA both in the test-tube and in living organisms. Preferred recombinases/recombination site combinations for use in the present invention are Cre-Lox, FLP-FRT, and R—RS, where Cre, FLP and R are recombinases from bacteriophage P1, yeast and *Zygosacharomyces rouxii* respectively, and Lox, FRT, and RS are the recombination sites. Other suitable systems include the attP and attB sites recognized by integrase of *Streptomyces* bacteriophage phiC31 site-specific recombination system. To be functional in plants, these sites require 7-8 base pairs (bp) of core sequence between 12-13 bp inverted repeats; the asymmetric core site determines the site orientation, and thus the types of recombination product. Regardless of whether recombination sites are placed on or within a single DNA molecule in direct or opposite orientation, or placed on unlinked linear or circular DNA molecules, the corresponding recombinase can catalyze the reciprocal exchange to produce a deletion, inversion, translocation or co-integration event. See, Bollag et al., *Ann. Rev. Genet.* 23:199-225 (1989); Kilby et al., *Trends Genet.* 9:413-421 (1993); and Ow, *Curr. Opinion Biotech.* 7:181-186 (1996). Examples of low frequency restriction sites e.g., for rare-cutting restriction enzymes and nucleases, include intron encoded yeast endonuclease I-SceI (Choulika et al., Mol. Cell. Biol. 15:1968-1973 (1995)), Ho nuclease of *S. cerevisiae*, Not1 (an 8 bp cutter) and 6 b.p. cutters with low number of recognition sites in plant genomes e.g., Sal1 and Cla1.

Another embodiment of the present invention is directed to cultures of plant cells containing chromosome fragments containing the exogenous DNA and that exhibit normal chromosomal activities. Another aspect of this embodiment is directed to transgenic plants regenerated or derived from the aforementioned cultures. Plants produced in accordance with the disclosed methods are genetically different from transgenics produced via known methods. The transgenic plants of the present invention contain the transgenes in a single locus and allow for the transgenes to move together as a single locus in a breeding program. Known methods, on the other hand, result in the random integration of the transgene in the plant genome.

The methods of the present invention may be practiced on a wide variety of plants. These include: maize, tomato, turfgrass, asparagus, papaya, sunflower, rye, beans, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, tulip, Douglas fir, cedar, white pine, scotch pine, spruce, peas, cotton, flax, coffee and members of the *Brassica* family such as canola and rape seed.

Although described thus far in the context of plant cells, the method of the present invention also is applicable to animal cells and animal artificial chromosomes. This embodiment entails introducing an exogenous nucleic acid e.g., DNA, into animal cells to produce a transformed animal cell, treating the transformed animal cells e.g., by irradiation or with chemical agents, to produce chromosome fragments; fusing the treated animal cells with non-transformed or undamaged animal cells that are the same or different from the transformed cells (preferably the same or a closely related animal such as from the same family); and identifying cells derived from the fused cells that contain chromosome fragments that exhibit normal animal chromosomal activities and wherein the exogenous nucleic is expressed.

The invention will be further described by reference to the detailed examples. These examples are provided for purposes of illustration only, and are not intended to be limiting unless otherwise specified.

EXAMPLES

This section contains three examples. Example 1 describes experiments conducted to demonstrate the production of stable microchromosomes following irradiation, fusion and plant regeneration. Example 2 demonstrates the production of stable artificial chromosomes that are able to confer selective advantage to the cells in which they are maintained and which contain yeast artificial chromosomes for conferring shuttle properties to the plant artificial chromosome. Example 3 is a method for visualizing the location of the introduced exogenous DNA in a plant cell and for the visualization of microchromosomes.

Example 1

Evidence for the Production of Stable Chromosome Fragments

Populations of asymmetric hybrids are produced by fusion with a radiation-inactivated donor. The manipulation of the introduced genetic variation could result in a quicker introgression of a desired trait. Therefore, this technique could be applied in breeding programs. In the asymmetric nuclear hybrids produced between distant and closely related species, the resulting plants were male sterile, even though they appeared to contain only a few chromosomes from the donor partner as shown in Famelaer, et al., Theor. Appl. Genet. 79:513-520 (1990). The scheme presented in FIG. 1 shows the basic strategy applied for the minichromosomes' production in plant cells.

Protoplast Isolation, Fusion, Selection, and Regeneration

Shoot cultures of the NR-deficient mutant, Nia26, of *N. plumbaginifolia* (2n 20, reversion frequency 4.04 10-7 (Dirks et al., Mol. Gen. Genet. 179:283-288 (1986)) were cultivated as described by Negrutiu, et al., Theor. Appl. Genet. 66:341-347 (1983). Shoot cultures of *N. sylvestris*, V-42 (2n=24, chlorophyll-deficient mutant), were cultivated on R'SA medium (Negrutiu, et al., Theor. Appl. Genet. 66:341-347 (1983)). Mesophyll protoplasts were isolated from both parents according to Negrutiu, Z. Pflanzenphysiol. 100:373-376 (1981). Donor protoplasts were irradiated in a Gamma cell 200 (Co60 source, dose rate 0.048 J kg-1s-1) with different doses, and fused with recipient cells according to Kao, in: Wetter, L R, Constabel F (eds.) Plant Tissue Culture Methods, NRCC 19876:49-57, (1982). Culture and selection conditions of protoplasts and fusion products were carried out according to Dirks et al., Mol. Gen. Genet. 179:283-288 (1986). Cell colonies were regenerated on RPO.25 or RP1 medium (Installe et al., J. Plant Physiol. 119:443-454 (1985)) with 0.25 mg or 1 mg/l zeatine. Regenerated plants were further cultivated on R'SA medium. Chromosome analysis of regenerated hybrids.

Chromosome analysis was facilitated by morphological differences of recipient and donor metaphase chromosomes: *N. plumbaginifolia* is characterized by telocentric and *N. sylvestris* by meta- or submetacentric chromosomes. Regenerants can be classified into two groups: a first group of 19 plants from 13 different cell colonies, with 43-56 chromosomes (37-42 recipient chromosomes), and a second group (2 plants from 2 independent cell colonies) with 61-67 chromosomes and a hexaploid set of recipient chromosomes. The average number of identifiable donor chromosomes in 15 independent regenerants is about 8.7. Donor chromosome fragments resulting from radiation-induced damage were observed in all plants.

The total number and exact type of chromosomes are difficult to establish for several reasons. First, small variations in chromosome numbers may exist within one regenerant. Also radiation damage of donor chromosomes may result in recipient-like chromosomes; and interspecific chromosome exchanges may result in reconstructed and deleted recipient chromosomes as well as in the loss of chromosomes. Finally, chromosome translocations could not be observed.

Fusion products between remote species generally spontaneously eliminate one of the parental genomes, thereby creating asymmetric hybrids that contain, in addition to a complete recipient genome, a few chromosomes derived from the donor. Methods for transferring part of the plant genome have been developed since one often wants to introduce only a small number of traits from the donor into the recipient. The donor-recipient method, also called "gamma" fusion, is the most frequently used technique for creating asymmetric somatic hybrids. Although irradiation directs the process of chromosome elimination, it is not the sole control of the process. Highly asymmetric hybrids in which only one or few donor chromosomes are contained, have only rarely been described. This observation is irrespective of the radiation dose use.

Minichromosomes Production in Asymmetric "Gamma" Hybrids Between *Nicotiana* and *Atropa*

Figure 2:
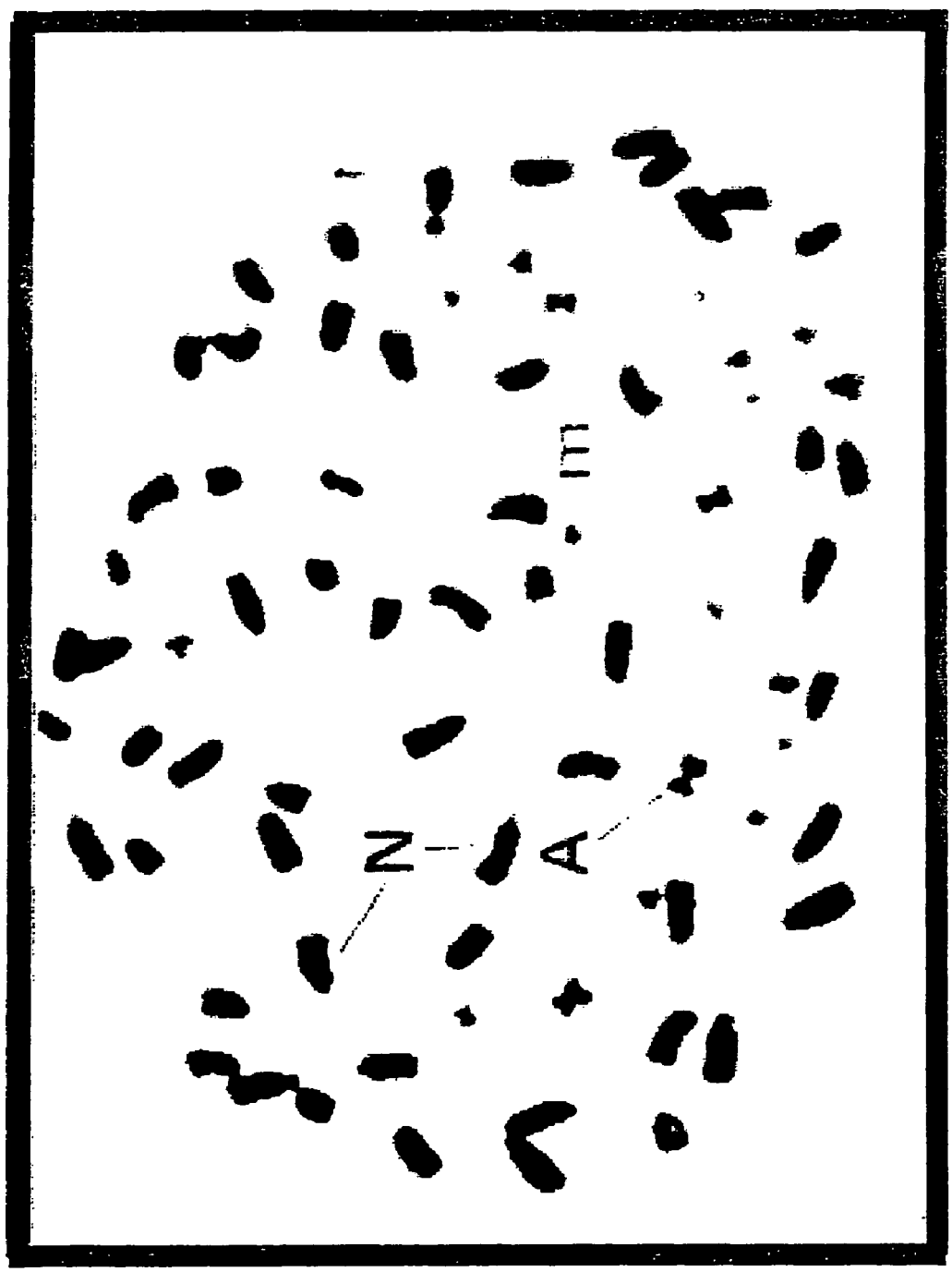
FIG. 2 is a photograph illustrating metaphase chromosomes of "gamma"-hybrid between *Nicotiana plumbaginifolia* and *Atropa belladonna*, wherein (N) represents *Nicotiana* chromosomes; (A) represents *Atropa* chromosomes; (m) represents minichromosomes produced by "gamma"-treatment of *Atropa* protoplast; and (r) represents reconstructed chromosome.

Nitrate reductase deficient mutant of *Nicotiana plumbaginifolia* (cnx20) and *Atropa belladonna* plants were used for the experiments. Protoplasts were isolated as described by Negrutiu et al., Theor. Appl. Genet 72:279-286 (1986). Treatment of *Atropa belladonna* protoplasts with different doses of gamma rays was performed as described by Gleba et al., Theor. Appl. Genet. 76:760-766 (1988). The fusions of protoplasts were carried out as described by Menczel et al., Genetics, 100:487-495 (1982). Protoplasts were cultured in K3 medium for 2 weeks, diluted in MDn medium (Negrutiu et al., Theor. Appl. Genet. 66:341-347 (1983); Negrutiu et al., Theor. Appl. Genet 72:279-286 (1986)). After 1 month visible calli were transferred to solid medium and regenerated as described elsewhere (Installe et al., J. Plant Physiol. 119:443-454 (1985)). Metaphase plates from root tips for chromosome analysis were prepared as described by Gleba et al., Theor. Appl. Genet 76:760-766 (1988). The chromosomes analysis was greatly facilitated as the *Atropa metaphase* chromosomes are approximately twice shorter and significantly thinner that *Nicotiana plumbaginifolia* chromosomes (Gleba et al., Theor. Appl. Genet 76:760-766 (1988)). Minichromosomes, which are significantly smaller than *Atropa* intact chromosomes, were detected in all samples analyzed. The size of detectable minichromosomes was variable starting from almost half the size of parental chromosome to hardly visible minichromosomes (FIG. 2). It is very possible that such "gamma" hybrids contain so small minichromosomes that they are simply invisible on the metaphase plate.

The constructs described in Example 1 suit many different purposes including plant minichromosome rescue in yeast cells and cloning any genes of interest. The genes of interest which could be cloned into the YAC would include, but not be limited to, genes for herbicide resistance, quality trait improvement such as starch modification, oil quality, protein quality, drought resistance, cold tolerance, pest resistance, and other input and output agricultural traits.

Any number of methods can be used to identify the integration sites of the YAC. These methods include RAPD to mapping, fluorescent in situ hybridization (FISH) and Southern analysis. By identifying constructs that have inserted near the centromere, there is a greater chance of recovering fragmented chromosomes containing the centromere region and the construct of interest. There is evidence that this minimal "chromosome" can be repaired in the cell to include telomeres. This biologically assembled artificial chromosome could be rescued by transformation into yeast and from them being used to re-transform other plants of the same species.

Example 2

Identification of Kanamycin Resistant Plants Following Irradiation and Asymmetric Fusion Isolation, Fusion and Culture of Protoplasts Mesophyll protoplasts were isolated from 4- to 6-week-old plants of *N. plumbaginifolia* (P2) and kanamycin-resistant *Petunia hybrida* (transformant VR2828×V23) as described by Negrutiu et al., Theor. Appl. Genet. 72:279-286 (1986). Before fusion kanamycin-resistant Petunia protoplasts were irradiated with gamma rays (100 krad) from a cobalt60 source. Fusions were carried out as described by Menczel et al., Genetics 100:487-495 (1982). The protoplasts were further cultured in K3 medium and subsequently diluted in selection medium (MDn) supplemented with 25 mg/l kanamycin monosulphate. After one to two months, visible calli were transferred to solid selection medium and subsequently regenerated as described by Installe et al., J. Plant Physiol. 119:443-454 (1985). Control experiments were carried out under the same conditions.

Cytological Analysis

For chromosome analysis, metaphase plates were prepared using the protoplast method as described by Mouras et al., Caryolgia 31:117-127 (1978). Alternatively, metaphase spreads were also obtained from the root tips of regenerated plants as described by Pijnacker et al., Can. J. Genet. Cytol. 26:415-419 (1984).

Hybrid Isolation

One to two weeks after fusion of wild-type *N. plumbaginifolia* (P2) protoplasts with irradiated (100 krad) kanamycin-resistant *Petunia hybrida* (transformant VR2828× V23) protoplasts, kanamycin monosulphate, at a concentration of 25 mg/l, was added to the culture medium. After a further culture of one to two months, green resistant calli were obtained at a frequency of about 10-4. This transformation frequency is in the range of "gamma"-fusion experiments. In total, 86 stable kanamycin-resistant calli were recovered and 24 (28%) could easily be regenerated into plants that resembled the recipient partner *N. plumbaginifolia*. Moreover, organogenic hybrid calli regenerated numerous shoots that were analyzed at the cytological, molecular and genetic levels. As expected, control experiments did not result at all in the production of resistant colonies on the selection medium.

A total of 14 lines have been analyzed by karyotypic analysis. In most of the lines only *Nicotiana* chromosomes were observed at the diploid or tetraploid level. However, in one diploid line and four lines that were nearly tetraploid, a few (2-3) chromosome fragments could be seen.

A number of asymmetric nuclear hybrid clones have been produced by the treatment of plant cells with lethal doses of irradiation and subsequent fusion experiments. From these results it seems that irradiation can be used to partially direct the process of chromosome elimination, and that the elimination is not only due to the mutagenic effect of the irradiation. This process results in completely fertile hybrid plants. The ability to obtain hybrid plants that were kanamycin resistant was dependent on the presence of the kanamycin gene in the irradiated donor. All of the regenerated plants resembled the recipient partner. In some lines the presence of a few chromosome fragments was demonstrated, which is probably created by the irradiation of the protoplasts.

Vectors for Minichromosome Tagging

In order to tag and rescue plant minichromosomes produced as described above, two different vector systems were used.

Figure 3:
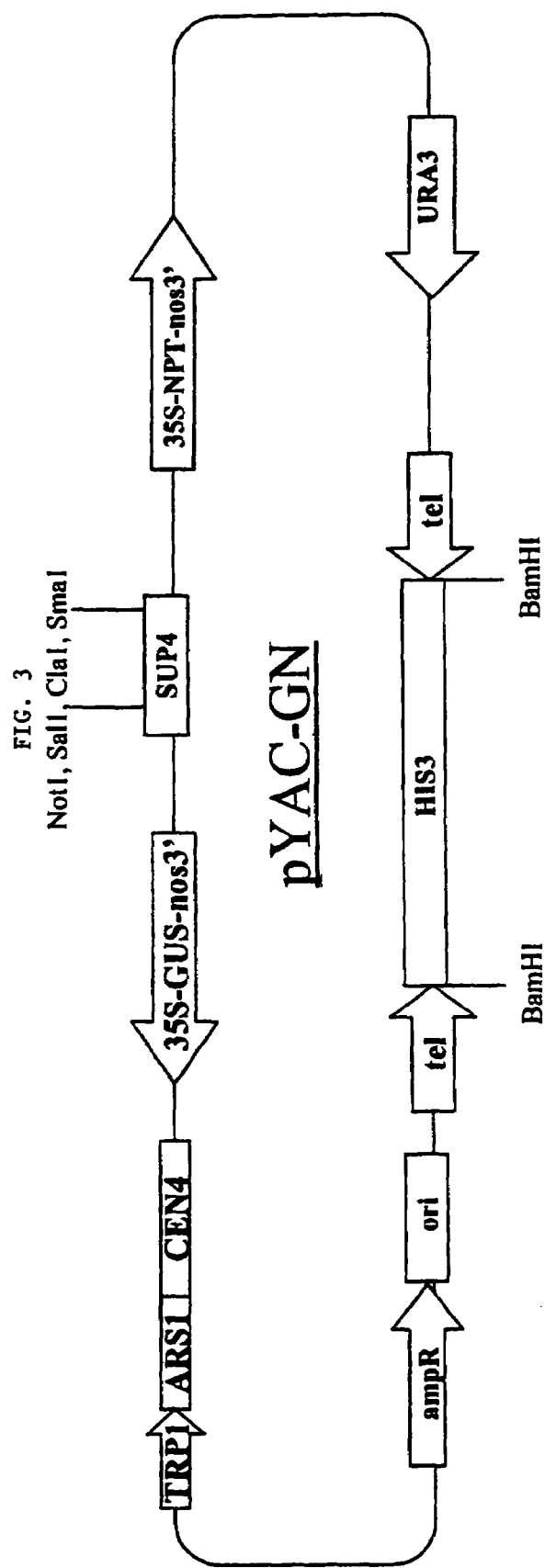
FIG. 3 is a plasmid map of plasmid pYAC-GN.

The first vector pYAC-GN is shown in FIG. 3. It was created from pYAC-4 by insertion of two genes: p35S-APH (3')III-NOS3' and p35S-GUS-NOS3' into Sal1 and Cla1 sites respectively. Transformed plants can be selected for kanamycin resistance as well as for GUS activity. A Polylinker containing rare-cutting for plant DNA sites was inserted into EcoR1 site of SUP4 gene. This polylinker can be used for further modification of pYAC-GN by inserting for example recombination sites recognized by site-specific recombinases, thus allowing integration of any gene(s) of interest into plant minichromosomes containing YAC-GN. The rest of the sequences in the construct are of pYAC 4 origin and can be used to resque plant minichromosomes in yeast cells.

Figure 4A:
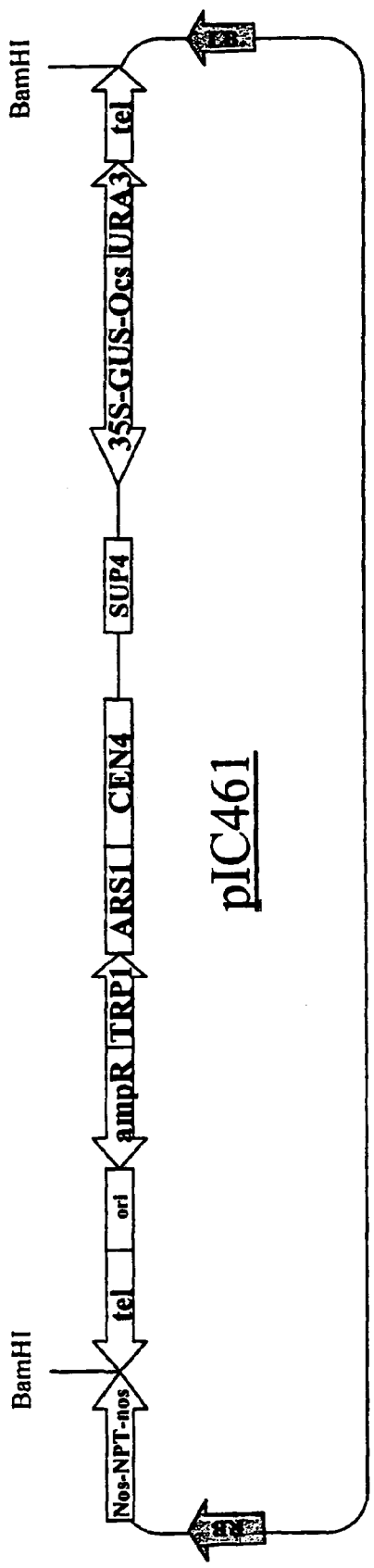
FIGS. 4A and 4B are plasmid maps of pIC461 and pIC462.
Figure 4B:
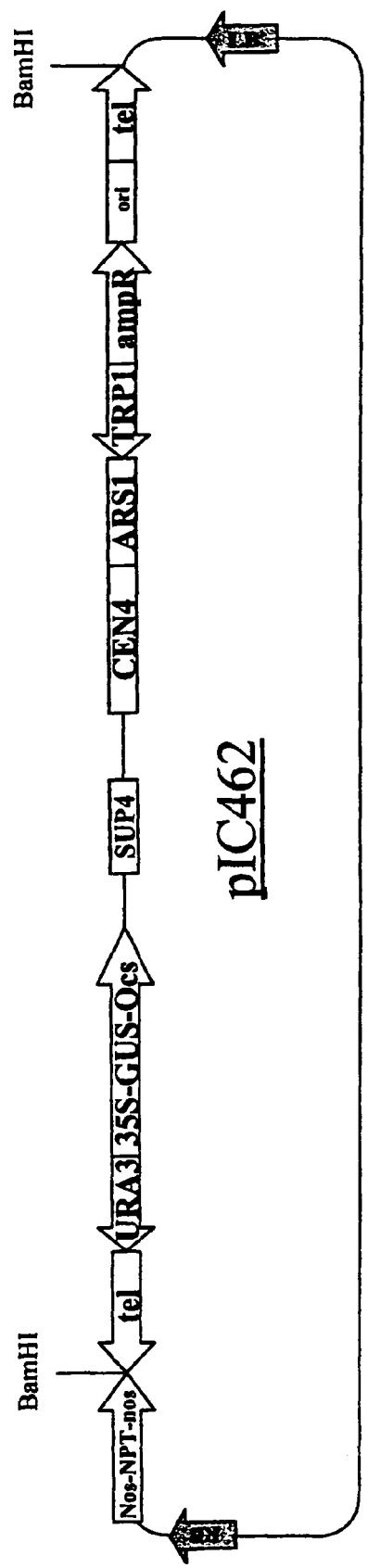

Two other vectors, pIC461 and pIC462 (FIG. 4) were made as described below. Expression cassette p35S:GUS: OCS3' was cloned into ClaI site of pYAC-4. Resulting plasmid was inserted into pBIN19 as BamHI fragment, producing pIC461 or pIC462 depending on orientation of insert. This vector allows *Agrobacterium*-mediated transformation of plant cells due to the presence of pNOS-NPTII-NOS3' gene within T-DNA borders.

Transformation of *Nicotiana* Species with YAC-Derived Constructs.

The vector pYAC-GN was used for direct transformation of *Nicotiana tabacum* protoplasts using a solution of PEG with $Ca^{2+}$ and pH 9.8. Seeds of *Nicotiana tabacum* cv Wisconsin were germinated on media MS after sterilization with solution "diacid" for 5 minutes and washing 5 times with sterile water. Three- to four-week old leaves were used for protoplast isolation. The protoplasts were transformed as described by Koop et al., Planta, 199:193-201 (1996). Leaves were cut on pieces and put abaxial side down on the surface of filter-sterilized enzyme solution containing Cellulose Onozuka 0.5%, Macerozime 0.5%, Dricelase 0.25%, Cellulysine 0.25%, 0.5 M mannitol and $CaCl_2*2H_2O$ 110 mg/l. The pH was adjusted to 5.7. After a 16 h incubation at 27° C. in the dark, leaf pieces were teased to release any protoplasts that had not been liberated by enzyme action alone. The protoplasts were sedimented by centrifugation (100×g, for 5 min) and washed in 0.5M sucrose, 15 mM $CaCl_2$ W5 solution was loaded onto the top to prevent damage of protoplasts from direct contact with the air. After centrifugation at 100×g for 5 min protoplasts were transferred to a new centrifuge tube and resuspended in 10 ml of TB buffer containing 0.4 M mannitol, 15 mM $CaCl_2$ pH 5.7. The density of protoplasts was adjusted to $5 \times 10^6$ protoplasts/ml. One hundred microliters of this suspension was transferred to 6 cm Petri dish and the protoplasts were left for a few minutes to settle. The DNA solution (25 μl of 50 μg pYAC-GN dissolved in 18 μl TE pH 5.6 plus 7 μl of culture media) was carefully added to the suspension, resuspended by gentle shaking of Petri dish and finally mixed with 125 μl of PEG solution (40% (w/v) of PEG 4000, 70 mM $Ca(NO_3)_2$, 1,2754 g mannitol per 26 ml). After 7-8 min of incubation the culture media was added to a volume of 125 μl, and after two minutes 2.6 ml of culture media was gradually added. After two weeks of incubation kanamycin was added to select transformed colonies. The *Agrobacterium*-mediated plant transformation was used with two other vectors—pIC461 and pIC462. Leaf-discs transformation of *Nicotiana sylvestris* and *Nicotiana tabacum* species was performed using standard protocol. Leaf disks were co-cultivated with *Agrobacterium tumefaciens* EHA105 harboring pIC461 or pIC462 in MS media complemented with 1 mg/l BAP and 0.5 mg/l NAA. After 24 hours leaf-discs were transferred onto solid MS media with 1 mg/l BAP, 0.1 mg/L NAA, 200 mg/L carbeniciline and 200 mg/L cefotaxime. After 7 days explants were transferred onto the same media but complemented with 25 mg/L kanamycin. After 2-3 weeks concentration of kanamycin was increased to 50 mg/l.

Generation of Minichromosomes by Irradiation of Protoplasts.

Protoplasts of primary transformants carrying pYAC-GN or T-DNA of either pIC461 or pIC462 were used for gamma-irradiation. Then gamma-irradiated protoplasts of *Nicotiana tabacum* were fused with protoplasts from the other. It was reported in Parokonny et al., Plant J, 2:863-874 (1992), that a number of stable minichromosomes originated from the irradiated parent was present in several regenerants. The purpose of this experiment, therefore, was to get the asymmetric somatic hybrid having a minichromosome with loxP site. Two irradiation doses were used—250 Gy and 500 Gy. The protoplast fusion technique performed was based on that of Negrutiu et al., Theor. Appl. Genet. 66:341-347 (1983). Leaves were cut on pieces and put abaxial side down on the surface of filter-sterilized enzyme solution containing Cellulose Onozuka 0.5%, Macerozime 0.5%, Dricelase 0.25%, Cellulysine 0.25%, 0.5 M mannitol, $CaCl_2*2H_2O$ 110 mg/l, 6 mg/l BAP and 2 mg/l NAA. The pH was adjusted to 5.7. After 16 h of incubation at 27° C. in the dark the protoplasts were pelleted by centrifugation (100 g, for 5 min.) and washed in the solution of 0.5M sucrose with 15 mM $CaCl_2$. W5 was loaded onto the top of suspension in order to prevent protoplasts from contact with air. Protoplasts were resuspended in 10 ml of W5 and irradiated. Irradiated protoplasts were mixed with non-irradiated protoplasts of *Nicotiana plumbaginifolia*. Approximately 0.5 ml of that mix were transferred to the 6-cm Petri dish and allowed to settle for 20 minutes. Equal volume of PEG solution [40% PEG 4000, 70 mM $Ca(NO_3)_2$, 1,2754 g mannitol per 26 ml (0.27M)] was carefully added Then 200 μl of W5 were added, incubated for 15-30 min. and mixed with another 2 ml of W5. After 20 minutes of incubation W5 was changed once and finally replaced with 3 ml of culture media. After two to three weeks of incubation, kanamycin sulfate was added to select hybrid colonies. The selected hybrids carried complete *Nicotiana plumbaginifolia* genome and minichromosomes with YAC sequences and kanamycine resistant gene.

The same procedure was applied to produce asymmetric somatic hybrids between irradiated protoplasts of *Nicotiana tabacum* and *Nicotiana sylvestris* transformed with pIC461, pIC462 or pYAC-GN and protoplasts of *Nicotiana plumbaginifolia*.

Example 3

Genomic In Situ Hybridization (GISH)

In the process of producing asymmetric somatic hybrids is necessary to unequivocally identify the alien DNA and recipient genome. Methods used in the past include the analysis chromosomal genes, marker genes, and species-specific repeat sequences. The use of cytogenetic markers to identify chromosomes in chromosomal segments was limited to chromosomes that differed significantly in size or morphology.

The use of genomic in situ hybridization in which total genomic DNA used as a probe can be used to determine the parental origin of chromosomal material in asymmetric hybrids as described in Parokonny et al., Plant Journal 2:863-874 (1992).

Experimental Procedures:

Plant Material

Shoot cultures of nitrate reductase-deficient mutants of *N. plumbaginifolia* (cnx 20 and Nia 26, both with 2n=20), and a chlorophyll-deficient mutant of *N. sylvestris* CV-42, 2n=24) were cultivated as described by Negrutiu et al. Theor. Appl. Genet. 66:341-347 (1983). An autotetraploid cytotype of *N. plumbaginifolia* (2n=4x=40), used as a control for in situ hybridization, was generated by somatic doubling from wild-type material. Wild-type *A. belladonna* introduced into in vitro culture was used as a control for dot blot hybridizations. All material was originally raised at the Institute of Cell Biology and Genetic Engineering, Kiev, and maintained in in vitro culture at the Jodrell Laboratory, Royal Botanic Gardens, Kiev.

Asymmetric somatic hybrids were obtained by cell fusion of leaf mesophyll protoplasts from the non-irradiated parent (recipient) with gamma-irradiated mesophyll protoplasts from the other (donor). Irradiation doses administered prior to fusion ranged between 10 and 1000 Gy. Regenerants originated from individual nuclear hybrid colonies of the different fusion combinations. Regenerant Oct-3 was a product of symmetric cell fusion between mesophyll protoplasts of *N. plumbaginifolia* cnx 20 and a lysine-overproducing mutant of *N. sylvestris* (ALC; Negrutiu et al., Theor. Appl. Genet. 68:11-20 (1981)), without prior irradiation of one of the parents (Famelaer et al., Plant Sci. 61:105-117 (1989)). Regenerants were cultivated as described by Negrutiu et al., Theor Appl. Genet. 66:341-347 (1983) and Korostash et al. Biopolymers and the Cell 7:55-62 (1991).

DNA Isolation

Approximately 0.5-1 mg of genomic DNA were extracted from three to four young leaves of *N. plumbaginifolia* cnx 20 and *N. sylvestris* V-42, using the minipreparation technique of Dvorak, et al., Theor. Appl. Genet 63:349-360 (1982).

Dot Blot Hybridization

Samples containing between 0.02 g and 0.4 g of genomic DNA were denatured in 0.4 M NaOH, 10 mM EDTA, boiled for 10 min. and neutralized in 3 M ammonium acetate (pH 7.0). These were loaded into different wells of a BioRad dot-blotter in a final volume of 100 1 each. Identical dilution series were prepared for DNA from *N. sylvestris, N. plumbaginifolia* and *A. belladonna*. Blots were hybridized with 0.5 g ml-1 biotinylated total genomic DNA from *N. sylvestris* v-42, using the method described by Parokonny et al., Plant J. 2:695-704 (1992). Labeled DNA was detected using the BRL DNA detection kit (Life Technologies).

DNA Probes

Total Genomic DNA

For use as a probe for GISH, 3 g of total genomic DNA were sheared by vortexing for 10-30 sec. before labeling as described below.

(TTTAGGG)n. A high molecular weight probe concatenated by the polymerase chain reaction (PCR) from a synthetic oligomer homologous to the consensus sequence of the *A. thaliana* telomeric repeat (5'-TTTAGGG-3'; Richards, et al, Cell 53:127-136 (1988)), was kindly supplied by A.V. Cox (Jodrell Laboratory, Royal Botanic Gardens, Kiev).

pTa71. A probe containing the 5.8S, 18S and 25S ribosomal genes, and part of the intergenic spacer from wheat (pTa71; Gerlach, et al., Nucl. Acids Res. 7:1869-1885 (1979)), recloned into pUC18, was kindly supplied by Dr Kevin Jones, Department of Botany, University of Reading.

DNA Probe Labeling

Probe DNA was labeled with biotin-14-dATP (Life Technologies, Paisley, UK) by nick translation, as recommended by the manufacturer. Unincorporated nucleotides were removed by spin dialyzing through a 200 1 Sepharose CL-6B (Pharmacia) column (Maniatis et al., *Molecular Cloning: A Laboratory Manual*. Cold Spring Harbor. Cold Spring Harbor Laboratory Press, 1982). If the probe was to be used for in situ hybridization, a 30× excess of sheared denatured salmon testis DNA was added at this stage. The mixture was then precipitated once in ethanol and reconstituted in 20 1 of TE (10 mM Tris-HCl, pH 8.0, 1 mM EDTA). Spotting an aliquot of labeled DNA onto nitrocellulose and detecting labeled DNA using the BRL DNA detection kit (Life Technologies) tested biotin incorporation.

Chromosome Preparations

Root tips were pretreated in 0.035% colchicine (Sigma, Poole, UK) for 1.5 hours at room temperature, fixed in 3:1 ethanol:acetic acid for up to 2 weeks at 4° C., and stored in 70% ethanol at −20 C. Root tips were squashed in 45% acetic acid on slides treated with Vectabond (Vector Laboratories, Peterborough, UK) to aid cell adhesion. Slides were stored desiccated at −20 C. for one to two weeks before processing. They were then immersed in 3:1 ethanol:acetic acid for 30 min. and absolute ethanol for 2×10 min., air-dried and treated with 50 g ml-1 of DNase-free RNase in 2×SSC for 2 hr. at 37° C. After dehydrating through an alcohol series, they were dried in a vacuum desiccator overnight at 4° C.

In Situ Hybridization

The method used for in situ hybridization was as described by Parokonny et al., Plant J. 2:695-704 (1992). The hybridization mixture consisted of 10% dextran sulphate, 50% formamide, 450 g ml-1 sonicated, sheared salmon sperm DNA and biotinylated probe to final concentrations of 15 g ml-1, 5 g m-1 and 200 ng ml-1, respectively, for GISH, (TTTAGGG)n and pTa71. Post-hybridization washes were in 2×SSC at 42 C, 50% formamide, 50% 2×SSC at 42° C. and 2×SS° C. at room temperature. Biotinylated DNA was detected with fluoresceinated avidin using one amplification with biotinylated anti-avidin D as described by Schwarzacher et al., Ann. Bot. 64:315-324 (1989). Unhybridized DNA was visualized by staining with 0.5 g ml-1 propidium iodide. Chromatin from both parents was detected by counterstaining with 2 g ml-1 diaminidophenylindole (DAPI). Fluorescence was viewed with an Axiophot microscope (Carl Zeiss, Oberkochen, Germany), using Zeiss filter block 9 (excitation 450-490 nm) for simultaneous detection of fluoresceinated avidin and propidium iodide, and Zeiss filter block 1 (excitation 365 nm) for DAPI.

GISH was used to localize, and from each parental species in metaphase spreads of asymmetric somatic hybrids. Each of 31 plants originating from a different nuclear hybrid was treated by GISH. The irradiated donor for 17 of these was *N. sylvestris* and the remaining 14 were *N. plumbaginifolia*. The chromosomes from *N. sylvestris* fluoresced yellow, and those from *N. plumbaginifolia* fluoresced red. By the color of their fluorescence the species origin in rearranged chromosomes could be determined unequivocally. By counterstaining with DAPI, minichromosomes were identified and the donor chromosome could be identified by the color of the fluorescence. In situ hybridization localized the telomeric repeat at the termini of all chromosomes. Signals for the telomeric region could also be seen on chromosomes in which large segments had been deleted following irradiation.

INDUSTRIAL APPLICABILITY

The present invention is applicable to agricultural biotechnology and in particular, to the manipulation of the plant genome to produce plant artificial chromosomes and the introduction of non-native nucleic acid into plants using the artificial chromosomes.

All publications mentioned in this specification are indicative of the level of skill of persons skilled in the art to which this invention pertains. All these publications are herein incorporated by reference to the same extent as if each individual publication was specifically and individually indicated as being incorporated by reference.

Various modifications of the invention described herein will become apparent to those skilled in the art. Such modifications are intended to fall within the scope of the appending claims.

The invention claimed is:

1. A method of making a plant artificial chromosome, comprising:
   (a) preparing recombinant protoplasts of a first plant species containing an exogenous nucleic acid, wherein said exogenous nucleic acid comprises at least one restriction site, and at least one recombination site recognized by a site specific recombinase;
   (b) irradiating the protoplasts of (a), thus producing chromosome fragments of chromosomes contained in the recombinant protoplasts;
   (c) fusing the recombinant protoplasts of (b) with protoplasts of a second plant species to produce fused protoplasts, wherein the first and second plant species may be the same or different; and
   (d) identifying fused protoplasts of (c) or cells derived from the fused protoplasts of (c) that contain chromosome fragments containing the exogenous nucleic acid, and that exhibit normal plant chromosomal activities.

2. The method of claim 1 wherein (b) comprises irradiating the protoplasts with gamma radiation.

3. The method of claim 1 wherein said identifying of (d) comprises pulsed field gel electrophoresis.

4. The method of claim 1 wherein said second plant species is the same as said first plant species.

5. The method of claim 1 wherein said second plant species is a member of the same family as said first plant species.

6. The method of claim 1 wherein said first plant species is a monocot.

7. The method of claim 1 wherein said first plant species is a dicot.

8. The method of claim 1 further comprising (f) regenerating a whole plant from the fused protoplasts or plant cells identified in claim 1(d).

9. The method of claim 1 wherein the exogenous nucleic acid comprises at least one coding region.

10. The method of claim 1 wherein the exogenous nucleic acid comprises at least one sequence comprising a yeast chromosomal element.

11. The method of claim 1 wherein the exogenous nucleic acid comprises a yeast artificial chromosome.

12. A method of preparing a transgenic plant comprising:
    (a) preparing recombinant protoplasts of a first plant species containing an exogenous nucleic acid, wherein said exogenous nucleic acid comprises at least one restriction site, and at least one recombination site recognized by a site specific recombinase;
    (b) irradiating the protoplasts of (a), thus producing chromosome fragments of chromosomes contained in the recombinant protoplasts;
    (c) fusing the recombinant protoplasts of (b) with protoplasts of a second plant species to produce fused protoplasts, wherein the first and second plant species may be the same or different;
    (d) identifying fused protoplasts of (c) or cells derived from the fused protoplasts of (c) that contain chromosome fragments that exhibit normal plant chromosomal activities; and
    (e) regenerating a whole plant from the protoplasts or cells identified in (d) that contain said chromosome fragments containing the exogenous nucleic acid, and that exhibit normal plant chromosomal activities.

13. The method of claim 10, wherein the yeast chromosomal element comprises a first centromeric sequence functional in a yeast cell.

14. The method of claim 13, wherein the chromosome fragments further comprise a second centromeric sequence functional in a plant cell.

15. A method of making a plant artificial chromosome, comprising:
    (a) preparing recombinant protoplasts of a first plant species containing an exogenous nucleic acid, wherein said exogenous nucleic acid comprises a selectable marker gene and at least one restriction site, and at least one recombination site recognized by a site specific recombinase;
    (b) producing chromosome fragments of chromosomes contained in the recombinant protoplasts;
    (c) fusing the recombinant protoplasts of (b) with protoplasts of a second plant species to produce fused protoplasts, wherein the first and second plant species may be the same or different; and
    (d) identifying fused protoplasts of (c) or plant cells derived therefrom that contain chromosome fragments that contain the exogenous nucleic acid and that exhibit normal plant chromosomal activities.

16. The method of claim 15, wherein the exogenous nucleic acid further comprises at least one yeast chromosomal element.

17. The method of claim 16, wherein the yeast chromosomal element comprises a first centromeric sequence functional in a yeast cell.

18. The method of claim 17, wherein the chromosome fragments comprise a second centromeric sequence functional in a plant cell.

* * * * *